(12) United States Patent (10) Patent No.: US 12,564,707 B1
Kato (45) Date of Patent: Mar. 3, 2026

(54) THERAPEUTIC EYE MASK

(71) Applicant: Brian Kato, Oak Forest, IL (US)

(72) Inventor: Brian Kato, Oak Forest, IL (US)

( * ) Notice: Subject to any disclaimer, the term of this patent is extended or adjusted under 35 U.S.C. 154(b) by 592 days.

(21) Appl. No.: 17/840,289

(22) Filed: Jun. 14, 2022

(51) Int. Cl.
| | |
|---|---|
| *A61M 35/00* | (2006.01) |
| *G02C 7/02* | (2006.01) |
| *G02C 7/10* | (2006.01) |

(52) U.S. Cl.
CPC ............. *A61M 35/10* (2019.05); *G02C 7/022* (2013.01); *G02C 7/10* (2013.01)

(58) Field of Classification Search
CPC .......... G02C 7/022; G02C 7/10; A61M 35/10; A61F 9/045; A61F 2007/0004
See application file for complete search history.

(56) References Cited

U.S. PATENT DOCUMENTS

| | | | | |
|---|---|---|---|---|
| 1,066,795 | A | 7/1913 | Chandler | |
| 4,790,031 | A * | 12/1988 | Duerer ...................... | A61F 9/04 |
| | | | | 128/858 |
| 5,940,886 | A * | 8/1999 | McCarthy Smith .... | A61F 11/12 |
| | | | | 2/9 |

| | | | | |
|---|---|---|---|---|
| 6,537,308 | B2 * | 3/2003 | Burkhart ................... | A61F 7/02 |
| | | | | 604/303 |
| 6,543,056 | B2 * | 4/2003 | Spiteri ...................... | A61F 9/04 |
| | | | | 2/15 |
| 8,109,964 | B2 * | 2/2012 | Payne ................... | A61F 13/124 |
| | | | | 607/109 |
| 10,285,862 | B2 * | 5/2019 | Belliappa ................. | A61F 9/04 |
| 12,029,681 | B2 * | 7/2024 | Bruder ...................... | A61F 7/02 |
| 2003/0056281 | A1 * | 3/2003 | Hasegawa .............. | A61N 2/002 |
| | | | | 2/206 |
| 2017/0252210 | A1 * | 9/2017 | Bruder ................... | A61F 9/045 |

FOREIGN PATENT DOCUMENTS

| | | | | |
|---|---|---|---|---|
| WO | WO-2012160496 A1 * | 11/2012 | ............... | A61F 7/10 |

* cited by examiner

*Primary Examiner* — Philip R Wiest
*Assistant Examiner* — Eric Rassavong
(74) *Attorney, Agent, or Firm* — Sanchelima & Associates, P.A.; Jesus Sanchelima; Christian Sanchelima

(57) ABSTRACT

A therapeutic eye mask including a mask assembly, an adjusting assembly, and a customization assembly. The mask assembly includes pressure elements. The pressure elements are built in a satin material. The pressure elements are used to press an under-eye region of a user. The adjusting assembly includes a head strap. The head strap is attached to the mask. The head strap can adjust its size. The customization assembly includes an additional mask and lenses. The additional mask has openings. The lenses are inserted in the openings to be mounted as blocking lenses, corrective glasses, or sunglasses.

6 Claims, 4 Drawing Sheets

THERAPEUTIC EYE MASK

BACKGROUND OF THE INVENTION

1. Field of the Invention

The present invention relates to a therapeutic eye mask and, more particularly, to a therapeutic eye mask which can apply pressure to the under-eye region of the wearer.

2. Description of the Related Art

Several designs for a therapeutic eye mask have been designed in the past. None of them, however, include a set of modular eyeglasses or sunglasses.

Applicant believes that a related reference corresponds to U.S. Pat. No. 10,667,95 issued for an eye mask with a head band which is used to provide a therapeutic treatment. Applicant believes that another related reference corresponds to U.S. patent application No. 2017/0252210 issued for a therapeutic mask for treatment of the eyes with an adjustable strap. None of these references, however, teach of a therapeutic eye mask that is comprised of a satin covered mask with an adjustable head strap which is placed over the wearer's eyes and is used to apply pressure to the under-eye region of the wearer.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a therapeutic eye mask that includes an adjustable head strap to adjust the invention to different sizes.

It is another object of this invention to provide a therapeutic eye mask that includes openings to insert different types of lenses to use the therapeutic mask as sunglasses, eyeglasses, or the like.

It is still another object of the present invention to provide a therapeutic eye mask that includes a soft satin covering to provide comfort to the user.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
FIG. 1 represents an isometric operational view of the present invention 10 wherein a user is wearing the eye mask 10.
Figure 2:
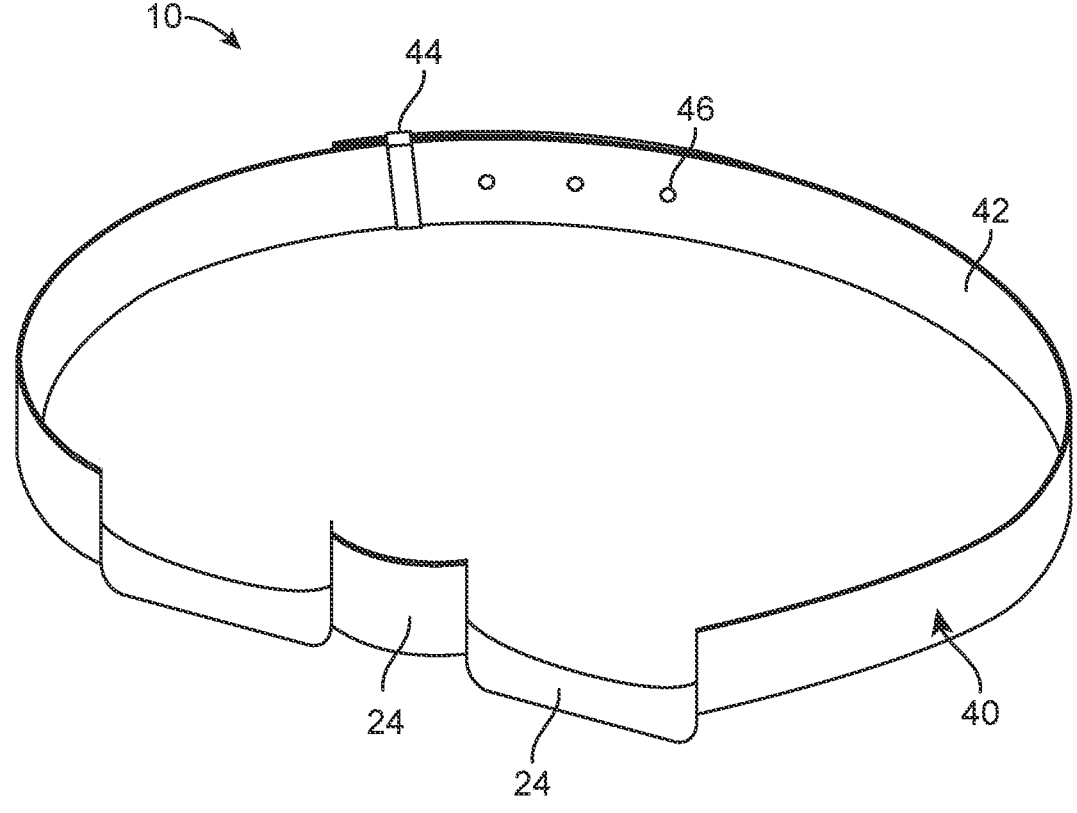
FIG. 2 shows an isometric view of the present invention 10. The present invention includes a mask assembly 20, an adjusting assembly 40 and a customization assembly 60.
Figure 3:
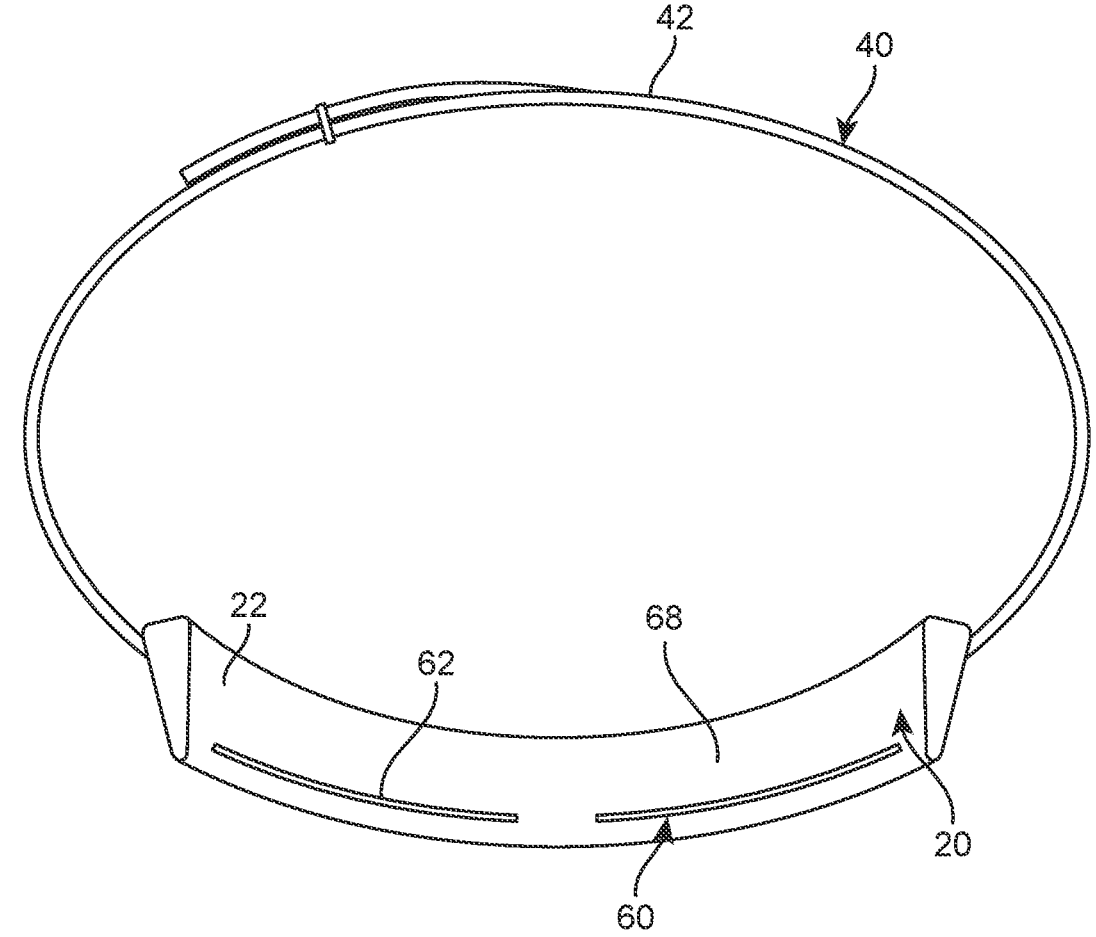
FIG. 3 illustrates a top view of the present invention 10.

Referring now to the drawings, where the present invention is generally referred to with numeral 10, it can be observed that it basically includes a mask assembly 20, an adjusting assembly 40 and a customization assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The mask assembly 20 may include pressure elements 24. The pressure elements 24 may be built in a satin and soft material such as cotton or rayon. It may be suitable for the pressure elements 24 to be built in rayon on the outside and cotton, flannel, or feather on the inside. In a preferred embodiment the pressure elements 24 may have a rounded shape that conforms with the shape of the under eye of a user. The pressure elements may be connected by a central element 22. The central element 22 is made of plastic, leather, or any other suitable material. The central element 22 may conform with the shape of the nose of a user. The pressure elements 24 may have a substantially curved shape that conforms with the lower eye contour. It may be suitable for the pressure elements 24 to be built with hydrogel or thermogel in the inside. It also may be suitable for the pressure elements 24 to contain collagen, hyaluronic acid, or vitamins. The pressure elements 24 may press the under-eye region of the wearer.

The adjusting assembly 40 may include a head strap 42 and an adjusting element 44. The head strap 42 may have a rectangle elongated shape that extends from the pressure elements 24 to a rear central portion to be worn as a head strap. The head strap 42 may be made of plastic, fabric, or any other suitable material. In a preferred embodiment the head strap 42 are two bands joined together through the adjusting element 44. The head strap 42 may be a corset head strap, an elastic head strap, knotted head strap or any other suitable head strap. The head strap 42 may be built in a satin and soft material such as cotton or rayon. It may be suitable for the head strap 42 to be built in rayon on the outside and cotton, flannel, or feather in the inside.

The adjusting element 44 may connect the head strap 42. The adjusting element 44 may be used to modulate the diameter formed by the junction of the head strap 42. The adjusting element 44 may be used to adjust the head strap 42 to the size of the head of the wearer. The adjusting element 44 may be used to press the mask 22 when used. The adjusting element 44 may be a knot, a belt, or any other suitable adjusting element 44 to adjust the size of the head strap 42. The adjusting element 44 may be made of plastic, leather, cloth, or any other suitable material.

Figure 4:
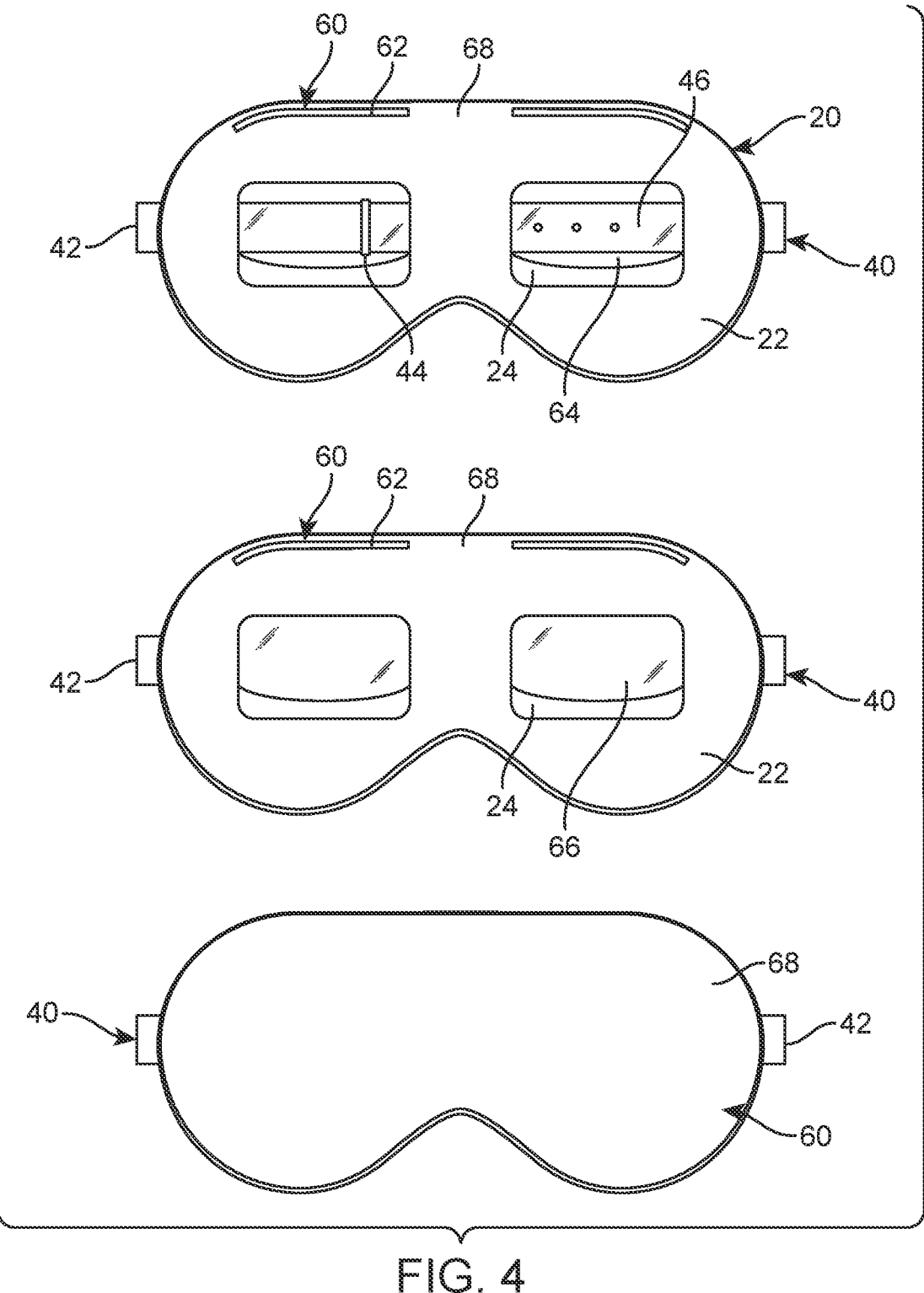
FIG. 4 is a representation of a front view of different embodiments of the present invention 10.

Referring now to FIG. 4 the customization assembly 60 may include openings 62, corrective lenses 64, non-prescription lenses 66 and a face cover 68. Openings 62 may be located on an upper edge of the face cover. In a preferred embodiment of the corrective lenses 64, the non-prescription lenses 66 may be inserted through the openings 62. In a preferred embodiment the pressure elements may be placed on the contour of the eyes. The adjusting element 44 may be used to adjust the head strap 42 to the user of the head. The pressure element 24 may press the under-eye region of the wearer to help in the treatment of eye bags or periorbital edema.

In one embodiment, corrective lenses 64 may be inserted through the openings 62. The face cover 68 may be mounted in the pressure elements 24. The corrective lenses 64 may be corrective lenses. Corrective lenses 64 are added to use said pressure elements 22 as corrective eyeglasses. Corrective eyeglasses are known in the prior art as lenses worn to correct defects of vision.

In another embodiment non-prescription lenses 66 are inserted through the openings 62 to be mounted in front of the pressure elements. The non-prescription lenses 66 are worn to provide protection against bright light, ultraviolet light, or any other kind of light. The non-prescription lenses 66 are not medical prescription lenses such as the corrective lenses 64. It may be suitable for the non-prescription lenses 66 to be yellow-tinted computer lenses, blue light blocking lenses, sunglasses lenses, protecting lenses or the like. The non-prescription lenses 66 may be added to the face mask to be used as non-prescription glasses.

In yet another embodiment the face covering 68 is a sleeping mask. In a preferred embodiment the face covering 68 may be built in a satin and soft material such as cotton or rayon. It may be suitable for the face covering 68 to be built in rayon on the outside and cotton, flannel, or feather in the inside.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A therapeutic eye mask, comprising:
   a head strap with an adjusting element that allows to secure distal ends of the head strap, said adjusting element adjusts a length of said head strap to contour to a user's head;
   wherein pressure elements are positioned along a curved section of the length of said head strap, wherein said pressure elements are secured together by a nose piece, also termed as central element, thereby creating a contoured engagement surface; wherein each pressure element has a substantially rectangular shape with a concave top edge and bottom rounded corners; wherein the concave top edge of the pressure elements extends lengthwise from a mid section of the nose piece to connect with a mid section of the head strap; wherein each pressure element extends downardly from said mid section of the head strap and nose piece until passing a bottom periphery of said nose piece and said head strap; wherein said pressure elements are built in satin material; wherein the substantially rectangular shape of the pressure elements featuring said concave top edge, is configured to be positioned over periorbital edema areas while leaving the user's eyes completely uncovered and unobstructed for normal vision and daily activities.

2. The therapeutic eye mask set forth in claim 1, wherein said therapeutic eye mask includes a customization assembly, said customization assembly includes a body which surrounds said pressure elements, said body has a symmetrical, horizontally elongated shape with two rounded eye-covering sections, wherein a lower edge of the body features a concave indentation at the center, wherein the upper edge is curved, wherein said customization assembly further includes lenses.

3. The therapeutic eye mask set forth in claim 2, wherein said body of said customization assembly includes two elongated openings along said upper edge, wherein each elongated opening is formed above each of said pressure elements, wherein said lenses are inserted into said body through said elongated openings; wherein when inserted, said lenses sit in front of said pressure elements.

4. The therapeutic eye mask set forth in claim 2, wherein said customization assembly further includes a cover that is configured to enclose said body when said therapeutic eye mask is worn as a sleeping mask.

5. The therapeutic eye mask set forth in claim 1, wherein said pressure element is built in a satin material.

6. A therapeutic eye mask, consisting of:
   a head strap with an adjusting element that allows to secure distal ends of the head strap, said adjusting element adjusts a length of said head strap to contour to a user's head;
   wherein pressure elements are positioned along a curved section of the length of said head strap, wherein said pressure elements are secured together by a nose piece, also termed as central element, thereby creating a contoured engagement surface; wherein each pressure element has a substantially rectangular shape with a concave top edge and bottom rounded corners; wherein the concave top edge of the pressure elements extends lengthwise from a mid section of the nose piece to connect with a mid section of the head strap; wherein each pressure element extends downardly from said mid section of the head strap and nose piece until passing a bottom periphery of said nose piece and said head strap; wherein said pressure elements are built in satin material; wherein the substantially rectangular shape of the pressure elements featuring said concave top edge, is configured to be positioned over periorbital edema areas while leaving the user's eyes completely uncovered and unobstructed for normal vision and daily activities.

* * * * *